United States Patent [19]

Lozano, Jr.

[11] Patent Number: 4,761,638

[45] Date of Patent: Aug. 2, 1988

[54] MEANS AND METHOD FOR DETECTING PRESENCE OF ELECTRICALLY CONDUCTIVE FLUID

[76] Inventor: Miguel A. Lozano, Jr., 1614 NW. 99th Ct., Des Moines, Iowa 50322

[21] Appl. No.: 907,063

[22] Filed: Sep. 15, 1986

[51] Int. Cl.⁴ ............................................. G08B 21/00
[52] U.S. Cl. .................................... 340/620; 340/604; 73/290 R; 324/65 R
[58] Field of Search ............... 340/604, 605, 620, 603, 340/618; 324/65 R; 73/290 R, 304 R

[56] References Cited

U.S. PATENT DOCUMENTS

| | | | |
|---|---|---|---|
| 3,757,316 | 9/1973 | Fiorenzo | 340/243 |
| 3,913,098 | 10/1975 | Nakamura et al. | 340/384 |
| 4,122,389 | 10/1978 | Haagen | 324/65 |
| 4,216,468 | 8/1980 | Kaufmann | 340/620 |
| 4,227,190 | 10/1980 | Kelley et al. | 340/604 |
| 4,268,824 | 5/1981 | Phillips | 340/604 |
| 4,279,078 | 7/1981 | Hinshaw et al. | 340/620 X |
| 4,319,232 | 3/1982 | Westphal et al. | 340/604 |
| 4,382,231 | 5/1983 | Miller | 340/620 X |
| 4,502,044 | 2/1985 | Farris et al. | 340/604 |
| 4,513,248 | 4/1985 | Miller | 324/439 |

Primary Examiner—Joseph A. Orsino, Jr.
Assistant Examiner—Jeffery A. Hofsass
Attorney, Agent, or Firm—Zarley, McKee, Thomte, Voorhees & Sease

[57] ABSTRACT

A means and method for detecting the presence of electrically conducting fluid whereby a signal is actuated upon the presence of fluid. The method of the invention includes placing two conducting members at the location to be monitored. A gating device having an electrical pathway to the signal device is actuated upon receiving sufficient biasing voltage. A voltage dividing network allows sufficient bias in voltage in two ways, either by the shorting of the two conducting members of the probe by electrically conducting fluid, or by the breaking of the circuit path between the electrical power source and the probe ends. The means of the invention utilizes a gating device having a biasing input connected to the middle of a voltage dividing network. Two conducting elements of a probe are attached to a point before the voltage dividing network and in the middle of the voltage dividing network respectively. A non-falsing circuit, a battery level circuit, and a remote alarm interface circuit can be added to the fluid detecting circuitry.

8 Claims, 2 Drawing Sheets

MEANS AND METHOD FOR DETECTING PRESENCE OF ELECTRICALLY CONDUCTIVE FLUID

BACKGROUND OF THE INVENTION a. Field of the Invention

This invention relates to a means and method for detecting the presence of an electrically conducting fluid, and in particular, to a means and method for actuating a signal upon detection of such fluid or upon tampering with the probe associated with the detection means and method.

b. Problems in the Art

There are many advantageous applications for a fluid sensing device. Among these are monitoring of basement water leakage, flood plains, fluid-carrying pipes or other fluid conveyors, and the like. Applications also exist for detection of thawing in freezers, malfunction of sprinkler systems, and remote monitoring of water levels.

It is essential that fluid detectors be reliable, accurate, and durable. Additionally, it is desirable that they be economical, adaptable for a variety of positionings and uses, and resistant to tampering and malfunction.

Numerous attempts have been made to produce a fluid detector for a variety of purposes. Many are complex and not economical. Others do not allow for placement of remote testing probes so that monitoring can be done from a central or convenient location.

Many present devices also are subject to tampering or malfunction without any means of notifying or signaling such an occurrence. For example, there are devices having a fluid-sensing probe comprised of two adjacent conducting members. Such devices signal the presence of fluid when the fluid bridges or shorts the two probe ends. However, this type of circuitry has inherent problems. If the electrical wires to the probe ends are cut, damaged, or otherwise broken or non-conductive, no signal will occur even if fluid is engaged across the probe ends. This is a tremendous deficiency in these currently used devices.

It is also important that maintenance be easy and economical, as well as the manufacture of these devices. Present devices are deficient in the complexity and cost associated with their parts, and in the periodic maintenance and checking required of those devices.

A still further deficiency of the present art is that it is many times advantageous to power the devices by batteries which are economical and allow placement of the devices in locations where household or commercial alternating current is not available. While many presently used devices are battery powered, their circuitry either consumes so much current that the battery life is limited, requiring frequent replacement of batteries, or, there is no monitoring of the strength of the batteries. Without this, the batteries could fail, either from use or deficiencies in the batteries, and the ability of the device to signal the presence of fluid would be lost. Furthermore, if the batteries' strength falls below a certain level, the circuitry may not function accurately.

Additionally, it would be advantageous to be able to interface a fluid detector, like the present invention, into existing monitoring systems, for example, home security alarm systems.

It is therefore a primary object of the present invention to provide a means and method for the detection of electrically conducting fluids which improves over or solves the deficiencies in the art.

A further object of the present invention is to provide an accurate and reliable fluid detector.

Another object of the present invention is to provide an accurate and reliable fluid detector which signals the presence of fluid.

Another object of the present invention is to provide an accurate and reliable fluid detector which signals if the probe associated with it or the wires connected to the probe are broken or tampered with.

A further object of the present invention is to provide an accurate and reliable fluid detector which prevents false signaling upon turning the device on.

A further object of the present invention is to provide an accurate and reliable fluid detector which is constantly powered, at low current levels, but includes a battery monitor which signals the decrease of the battery's strength below a preset level.

A still further object of the invention is to provide an accurate and reliable fluid detector which allows placement of a passive fluid detecting probe at substantial distances from the circuitry of the device.

A further object of the invention is to provide an accurate and reliable fluid detector which allows placement at or in normally or relatively inaccessable locations, and at remote, unattended sites.

Another object of the present invention is to provide an accurate and reliable fluid detector which can be interfaced into a variety of conventional monitoring or security alarm systems.

These and other objects, features and advantages of the invention will become more apparent with reference to the accompanying specification and claims.

SUMMARY OF THE INVENTION

The present invention includes a means and method for signaling the detection of electrically conducting fluid. The invention improves upon the present art by utilizing control circuitry which includes a passive probe having two adjacently positioned conducting elements. The probe can be positioned as desired and can be extended from the control circuitry by electrical cable to substantial lengths.

The control circuitry includes a gating device to present an electrical path from the power source to a signaling means. The gating device opens the electrical path upon the introduction of biasing voltage above a preset level. A voltage dividing circuit is utilized to determine when the gating biasing voltage is sent to the gating device. When no electrically conducting fluid is shorted across the probe conducting members, the voltage dividing network produces a voltage level underneath the biasing level for the gating device. However, when fluid shorts the probe ends, a portion of the voltage divider is bypassed and sufficient biasing voltage is introduced to the gating device to signal the alarm.

A modification to the basic invention includes adding a third conducting member to the probe end. The third conducting member is shorted directly to one of the conducting members and an electrical wire is extended back through the probe cable to the circuitry. A capacitor is placed in series with the wire connected to the third probe end. The third wire and probe end cause biasing voltage sufficient to open the electrical path through the gating means and actuate the signal if it is broken or otherwise disassociated. Therefore, any tampering or breaking of the cable to the probe is signalled.

Additionally, the capacitor prevents any aberrated signal through the probe wires or at the conductive members of the probe from falsing the gating means into conducting to the signal means.

The present device therefore allows reliable operation of the fluid detector at remote locations without continual manual checking of the connecting cable and probe ends. It also allows for very precise and accurate detection of fluids by the utilization of the voltage dividing network which can be set to high sensitivity.

Because of the unique characteristics of the present invention, it can be advantageously utilized in numerous applications. Because of its accuracy, reliability, and economy, the probe can be placed at remote, unattended areas, or in otherwise inaccessible locations. Examples are in between walls or floors, in drainage pipes or storm sewers, in the holds of boats or ships, etc. Remote, unattended placement can include multiple locations along rivers or flood plains, in irrigated fields, around reservoirs, etc. By placing a number of the detectors at significant locations, flash flood warnings can be more accurately and instantaneously predicted. Other possible uses include, but are not limited to, bedwetting monitors, and use with quadriplegics, utilizing moisture in their mouths to create signals which can communicate. The present device can even be made portable to be carried on a person as an emergency indicator if the person fell overboard from a boat or ship.

A still further modification includes the addition of circuitry to monitor the level of the battery used in the circuitry. When the battery's strength falls below a selected level, the signal is actuated. Therefore, reliability of the device is further enhanced.

An additional modification includes circuitry which allows the basic fluid detecting invention to be interfaced with a variety of types of other monitoring systems, such as home security alarm systems. Alternatively, the additional circuitry could be used to add a remotely located alarm, or plurality of alarms.

DETAILED DESCRIPTION OF THE PREFERRED EMBODIMENT

Figure 1:
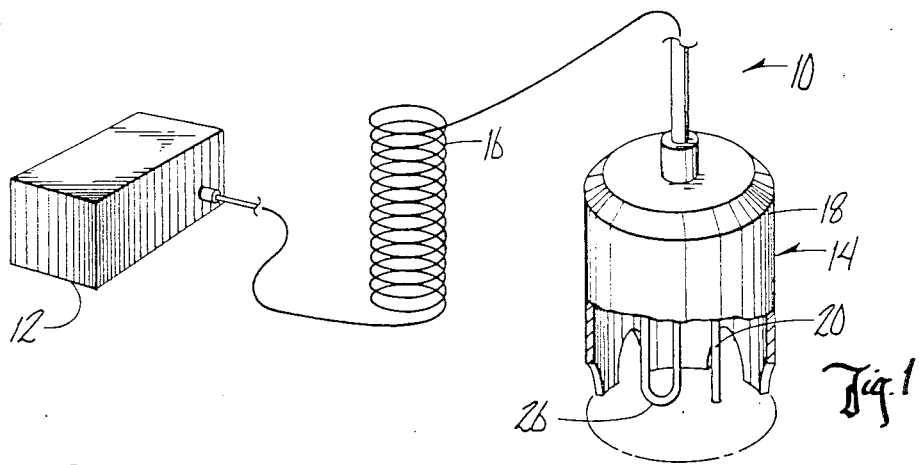
FIG. 1 is a schematic view of the invention depicting an enlarged, partially cut-away probe.

In reference to the drawings, and particularly FIG. 1, there is shown a fluid detector 10 in accordance with the invention. A housing 12 contains the control circuitry and electronic components for detector 10, except for the fluid detecting probe 14 and its connecting cable 16. The invention is such that probe 14 can be positioned remotely from housing 12 and still operate reliably and sensitively.

Connecting cable 16 can be many hundreds of feet long, and may even be longer. It is to also be understood that connecting cable 16 can be as short as desired. This adaptability of cable length allows flexibility in the use of detector 10. It can be advantageously used in situations where only a short cable 16 is required, such as in the home or for other confined purposes. At the same time, it can be advantageously used in applications where extremely long cable lengths are required, such as for remote flood detectors or leakage detectors for long pipes or in large buildings. This also allows numerous probes 14 to be placed at remote locations and have the housings 12 centrally located so that one person can monitor the same.

By incorporating all the electronic circuitry except for the probe and connecting cable into housing 12, reliability and durability is increased by centralizing the components which are most susceptible to damage by elements or other intrusion or interference. Maintenance is also greatly simplified.

Figure 2:
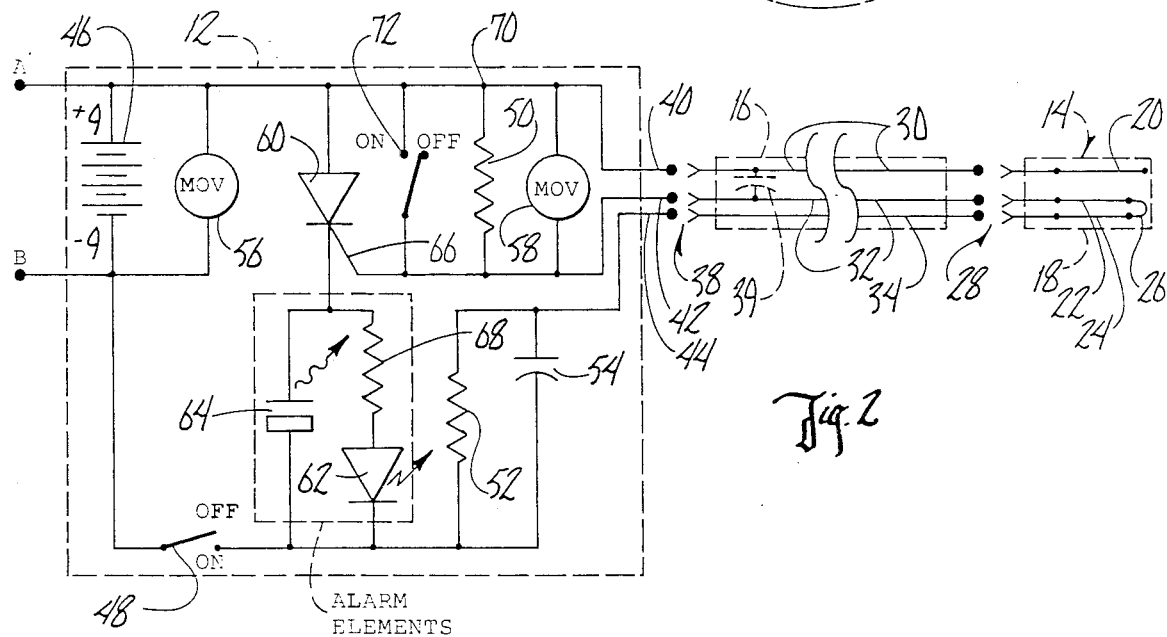
FIG. 2 is an electrical schematic of the fluid detecting circuitry.

By referring to FIG. 2, the exact circuitry of a preferred embodiment of the detector 10 can be seen. The circuitry involved with housing 12, probe 14, and connecting cable 16, are contained within the respectively referenced dashed line boxes.

Probe 14 consists of a hood 18 (see FIG. 1) which encircles three exposed conducting elements 20, 22, and 24. Conducting elements 23 and 24 are shorted or directly connected by the shorting element 26. Conducting elements 20, 22 and 24 are spaced apart from each other, but are closely adjacent. They can take on various configurations, but in the preferred embodiment, are elongated wires. Connecting elements 20 and 22, in the preferred embodiment, are approximately one-fourth of an inch apart, but other distances are possible.

Probe 14 enables the detection of conducting fluid by forming a conduction path from conducting element 20 to conducting elements 22 and 24 when electrical conducting fluid bridges or shorts those conducting elements. Therefore, in operation probe 14 is placed in such a position and orientation to most optimally detect fluid. Various types of configurations of hood 18 are possible.

Each of conducting elements 20, 22, 24, are connectable to cable wires 30, 32, and 34, respectively, at electrical junctions 28. Cable wires 30, 32, 34 of connecting cable 16 are independent of and insulated from one another, and insulated and protected from the outside environment by an appropriate cable cover. In the preferred embodiment, connecting cable 16 can be comprised of a twisted-pair, shielded cable (three conductor). As was previously stated, the length of cable wires 30, 32, 34 within connecting cable 16 can vary from being very short to very long, according to desire.

Each cable wire 30, 32, and 34 is in turn connectable through individual electric junctions 38 to input lines 40, 42 and 44, respectively. Input lines 40, 42 and 44 communicate connecting cable 16 and probe 14 to the electronic control circuitry contained within housing 12.

In the preferred embodiment, the circuitry is powered by DC (direct current) battery 46 having a rating of nine volts DC. On/off switch 48 is connected in series to battery 46, and when put to the "on" position, forms an electrical circuit through battery 46, resistor 50, input lines 42 and 44, cable wires 32 and 34, conducting elements 22 and 24, shorting element 26, resistor 52, and on/off switch 48. Additionally, during the initial turning "on" of on/off switch 48, capacitor 54, being connected in parallel across resistor 52, is charged. Metal oxide varistor (MOV) 56 is connected in parallel across battery 46 and MOV 58 is shorted across input lines 40 and 42. The function of MOV's 56 and 58 is to prevent damage to the device by induced voltages likely to be caused by nearby lightning strikes anywhere along the cable 16 from the device 10 to the probe 14. In addition, falsing, due to said lightning strikes is prevented. It is to be understood that MOV's 56 and 58 are optional only and are not required for the operation of the basic detection circuitry.

Detector 10 is enabled at this point. As can be seen in FIG. 2, a silicon controlled rectifier (SCR) 60 is connected in series with the parallel combination of a light emitting diode (LED) 62, and an audible signal device 64; all being connected in parallel with battery 46 and resistors 50 and 52. A biasing or triggering input 66 to SCR 60 is connected to the negative side of resistor 50. It is also noted that a resistor 68 is connected in series with LED 62 between SCR 60 and LED 62.

In this configuration, resistors 50 and 52 form a voltage dividing network. When the on/off switch 48 is turned "on", current flows through both resistors 50 and 52. The resulting voltage drop in the circuitry limits the amount of voltage entering biasing input 66 below the level at which SCR 60 opens an electrical pathway through LED 62 and audible signal device 64. Thus, LED 62 or audible signal device 64 do not actuate until the occurrence of one of two events.

First, if electrical conducting fluid bridges or shorts connecting element 20 with conducting elements 22 and 24, a low resistance current pathway will be formed bypassing resistor 50. Therefore, the voltage drop throughout the circuitry will be decreased raising the voltage at biasing input 66 to a level above that at which SCR 60 allows an electrical pathway to LED 62 and audible signal device 64. Therefore, both a visual and an audible alarm will actuate indicating the detection of electrical conducting fluid at probe 14.

The second method by which LED 62 and audible signal device 64 will actuate is if there is tampering or breakage of probe 14, connecting cable 16, or input lines 40, 42, or 44. This can happen if probe 14 is disconnected, if conducting cable 16 is disconnected from input lines 40, 42 or 44, or if the conduction path anywhere along input lines 42, 44, cable wires 32, 34, conducting elements 22, 24, or shorting element 26 is broken. In that event, the current path through both resistors 50 and 52 will be broken, causing sufficient current to enter biasing input 66 to open the path for electrical current through SCR 60. This provides a fail-safe feature for detector 10. Any tampering or damage to the probe or cable will cause signaling by detector 10 to alert monitoring personnel to this fact. It is pointed out that using a twisted-pair, shielded cable for connecting cable 16 enhances this feature so that damage to connecting cable 16 would most certainly cause LED 62 and audible signal device 64 to actuate.

A "phantom" capacitance was found to exist between input lines 40 and 42. This capacitance is actually the capacitance of cable 16 itself, and is depicted schematically in ghost lines by a capacitor 39 connected between cable wires 30 and 32 in FIG. 2. In the preferred embodiment, cable 16 is a Belden 8451 cable. The capacitance of that cable equals 34 pico-farads ($34 \times 10^{-12}$ farads) per foot of cable.

It has been found that a relationship exists between the resistance of resistor 52 (referred to as $R_{52}$), the capacitance of capacitor 54 (referred to as $C_{54}$), the resistance of resistor 50 (referred to as $R_{50}$), and the capacitance of cable 16. This capacitance (which will be referred to as $C_{cable}$), is represented by phantom capacitor 39 in FIG. 2 and is expressed in the following equation:

$$C_{54} = 4(R_{50} \cdot C_{cable})/R_{52}$$

It can therefore be seen that the minimum value of $C_{54}$ is such that the time constant of $R_{52}$ and $C_{54}$ must be at least four times the time constant of $R_{50}$ and $C_{cable}$. By knowing this relationship, selection of the values of capacitor 54, in light of the values of resistors 50 and 52, can be accomplished to insure proper sensitivity of the detector, regardless of the length of cable 16.

The preferred embodiment can also include an alarm test circuitry by connecting in parallel around SCR 60 a test switch 72 between connection point 70 and biasing input 66. Test switch 72 can be periodically moved to the "on" position to insure that SCR 60, LED 62 and audible signal device 64 are operational.

Under the arrangement of the present invention, probe 14 is passive until electrical conducting fluid is detected. Battery life under this system is substantially prolonged as compared to non-passive probes. The alarm test circuitry allows easy verification of the operability of the alarm components and of the SCR even though probe 14 is passive. It is to be understood that this connection of probe cable 16 would test the integrity of the supervisory circuit to the probe formed by shorted conducting elements 22, 24, and cable wires 32 and 34.

In the preferred embodiment shown in FIG. 2, SCR 60 can be a conventional SCR known within the art, and in particular, can be a small signal SCR having a product number SK3638/5402, being available from the RCA Company. A SCR is selected for its accuracy, sensitivity, and reliability of triggering, and being a bipolar solid state device, it is least suspect to damage or malfunction from trauma, lightning, and other problems.

In a preferred embodiment, resistor 50 is a one megohm resistor, whereas resistor 52 is a 150 kilohm resistor. LED 62 can be any mini-LED such as is known in the art; in the preferred embodiment LED 62 is rated at 20 milliamps. Resistor 68 is rated at 220 ohms. By incorporating resistor 68 in series with LED 62, almost any type of audible signal device 64, within reasonable specifications compatible with nine volt circuitry, can be used. In the preferred embodiment, audible signal device 64 is a "piezo-electric" beeper horn which is available from a variety of vendors. It is to be understood other similar types of audible signal devices could be substituted.

Capacitor 54 is an optional modification to the basic circuitry of detector 10. The function of capacitor 54 is to absorb or buffer the effect of any reflected voltage pulse from any part of connecting cable 16 or probe 14 when the circuitry is initially turned on. Without capacitor 54, there is a danger that such a reflected pulse might falsely actuate SCR 60 and incorrectly actuate the signaling devices. The specifications for capacitor 54 vary with the length of connecting cable 16. For example, in the preferred embodiment, capacitor 54 is a 0.022 microfarad capacitor when connecting cable 16 is 100 feet long. However, capacitor 54 should be a one microfarad capacitor for a 700 foot connecting cable 16. It is to be understood that capacitor 54 merely establishes the maximum length of cable 16 while not limiting, in any way, the minimum length of the cable. Capacitor 54 also beneficially allows the detector 10 to be insensitive to power fluctuations between as much as approximately 7.5 volts and 11.5 volts. The detector would also function on any power source between those two voltages.

It is to be understood the values of resistors 50 and 52 can be varied to change the sensitivity of detector 10. Furthermore, for different SCRs 60, resistors 50 and 52 may have to change in their resistance values.

Figure 3:
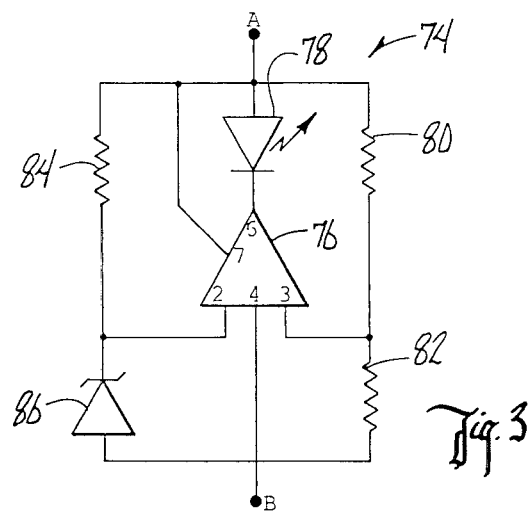
FIG. 3 is an electrical schematic of the battery monitoring circuitry which can be integrated into the circuitry of FIG. 2.

An additional modification to the circuitry of FIG. 2 can be made by adding the circuitry of FIG. 3 to it. FIG. 3 schematically depicts the circuitry for a battery monitoring subcircuit 74. Electrical connections A and B in FIG. 3 would be electrically connected to electrical connections A and B in FIG. 2. An operational amplifier 76 (op amp 76) has a 20 milliamp LED 78 connected to its output at op amp connection No. 6. Resistors 80 and 82 form a bridge circuit to divide the nine volts DC into a voltage which is dependent upon the voltage in the circuit depicted in FIG. 2. This voltage is introduced into the variable input of op amp 76 (op amp connection No. 3). Resistor 84 and Zener diode 86 are used to divide the voltage from the circuitry of FIG. 2 into a reference voltage across Zener diode 86. This reference voltage is inputted into op amp connection No. 2. Op amp connection No. 4 is connected through connection B to the negative side of battery 46, whereas op amp connection No. 7 is connected between electrical connection A and the positive side of resistor 84 and battery 46.

In this configuration, op amp 76 functions as a differential voltage comparator. In the preferred embodiment, resistor 80 is rated at 6.5 megohms whereas resistor 82 is rated at 2.2 megohms. Resistor 84 has a rating of 150 kilohms, whereas Zener diode 86 is a General Electric Zener diode rated at 4.3 volts. In this configuration, LED 78 is actuated when the voltage at op amp connection 3 drops to 8.15 volts DC with a maximum brilliance at 7.01 volts DC.

Thus, whether by virtue of battery 46 becoming weakened over a period of time or by abnormal discharge, battery monitoring subcircuit 74 will signal monitoring personnel of the condition so that detector 10 will continuously operate reliably. This also prevents a major deficiency in prior art devices in that if the battery fails, without continuous checking and testing, the entire system is disabled without knowledge.

Op amp 76 can be Model No. 741 integrated circuit manufactured by National Semi-Conductor and available from other manufacturers and distributors. It is to be understood that battery monitoring subcircuit 74 can be used with circuitry of FIG. 2, but that the circuitry of FIG. 2 will function for fluid detection purposes with or without battery monitoring subcircuit 74.

Figure 4:
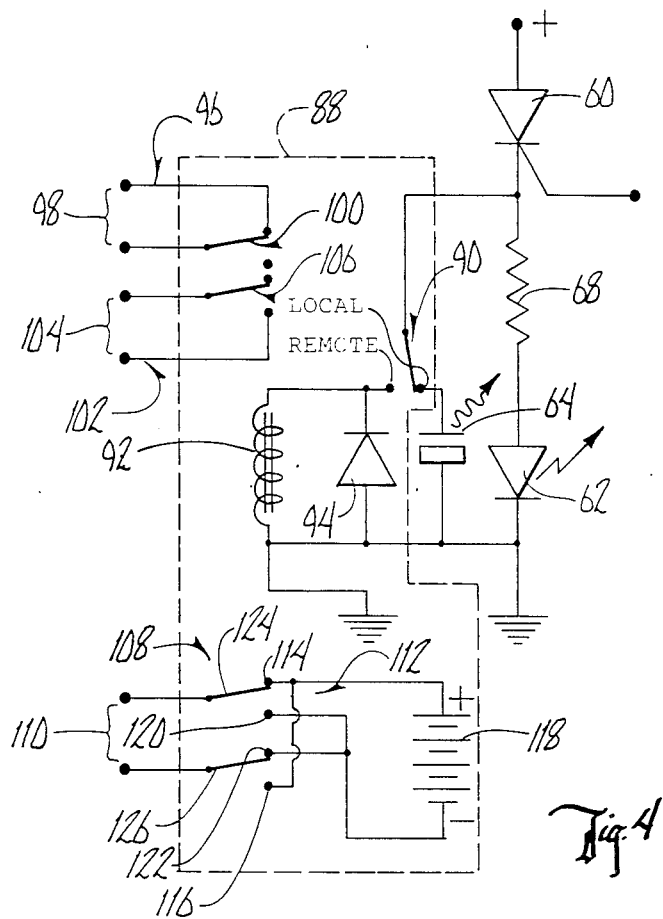
FIG. 4 shows an embodiment of additional circuitry integrated with the fluid detecting circuitry of FIG. 2 for interfacing remote alarms.

A further advantageous modification to the basic detection circuitry shown generally in FIG. 2, is shown in FIG. 4. A remote alarm interface circuit 88 could be integrated into the circuitry of FIG. 2. FIG. 4 shows SCR 60, resistor 68, LED 62, and audible alarm device 64 to represent the circuitry of FIG. 2. Other parts of the detection circuitry of FIG. 2 are not shown. The remote alarm interface circuit 88 can serve a number of functions. First, it can allow the detection circuitry of FIG. 2 to be hooked to a remote alarm (not shown). Secondly, although the remote alarm could be something the same or similar to LED 62 or audible alarm device 64, it could also be an existing home security alarm system. Thus, for example, if detector 10 were utilized in a home or building, it could be interfaced to an alarm in a security system in the building.

The preferred embodiment of remote alarm interface circuit 88, as shown in FIG. 4, includes a local/remote switch 90 connected between the output of SCR 60 and the input to audible alarm device 64. A four pole, double throw relay 92 is connected between local/remote switch 90 and the output to audible alarm 64. Additionally, a diode 94 is connected in parallel across relay 92. The side of relay 92 opposite local/remote switch 90 is connected to the negative side of battery 46, which is depicted in FIG. 4 as "ground". Local/remote switch 90 is a single pole, double throw switch. When switch 90 is positioned as shown in FIG. 4 to "local", the fluid detection circuitry functions as described with respect to FIG. 2. That is, upon detection of electrical conducting fluid, audible alarm device 64, and LED alarm 62 would be actuated. The same would occur if cable 16 or probe 14 were disconnected or damaged.

However, by moving switch 90 to the remote position, the audible signal device 64 would be bypassed and any signal passing through SCR 60 would be routed to relay 92 instead. The relay would in turn pass the signal on to actuate the remote alarm device.

FIG. 4 shows that the remote alarm interface circuit 88 can contain a variety of different connections to be used with remote alarms. For example, most common security alarm systems utilize three basic alarm actuating circuit schemes. First, some use a normally closed supervisory loop such as shown at 96. Electrical connections 98 would be connected to the alarm circuitry. In this scheme, the alarm would not sound as long as the normally closed supervisory 96 is closed. However, when normally closed switch 100 would be moved to an opened position by actuation of relay 92, circuit 96 would be opened thus actuating the alarm.

A second security alarm scheme involves a normally open supervisory loop 102. Electrical connections 104 are connected to the alarm device. Switch 106 is kept in a normally open position, as shown in FIG. 4. However, when relay 92 is energized, switch 106 closes which causes the alarm device to be actuated.

A third security alarm scheme is also shown in remote alarm interface circuit 88. A high security, polarity-reversal supervisory loop arrangement 108 is used by some security systems to actuate their alarms. Electrical connections 110 are connected to the alarm device. A four pole, double throw switch 112 has two poles 114 and 116 connected to the positive side of battery 118, with the two other poles 120 and 122 connected to the negative side of battery 118. Actuation of relay 96 causes switch contact 124 to change connection between positive pole 104 to negative pole 120, and contact 126 to change connection from negative pole 122 to positive pole 116. Thus, polarity going to security alarm device 110 is changed causing actuation of the security alarm.

It can therefore be seen that remote alarm interface circuit 88 can be composed of one or more of the different security alarm actuation schemes described above. Other schemes can be utilized, such as are well within the skill of those within the art.

It is to be understood that diode 94, in the preferred embodiment, can be any type of small signal diode, here being a diode type (1N914). Diode 94 is necessary to "buck" the inductive kick-back voltage generated when relay 92 is de-energized.

The included preferred embodiment is given by way of example only, and not by way of limitation to the invention, which is solely described by the claims herein. Variations obvious to one skilled in the art will be included within the invention defined by the claims.

For example, the detector and battery monitoring circuitry could be powered by alternating current; or any DC battery power could be continuously recharged by any of a variety of conventional means, including solar power. The combined circuitry of the preferred embodiment shown in FIGS. 1 and 2 draws less than 1 (one) milliamp of current and therefore should allow conventional long life batteries to be effective for six to eight months. The detector circuitry of FIG. 1 alone draws only 50μA (fifty microamps), whereas the battery monitoring circuit of FIG. 2 draws ⅓ mA (one-third milliamp)

Also, it is to be understood that other electrical components could be utilized to perform the same functions as those disclosed herein. Light emitting diodes 62 and 78, and audible signal device 64, could be replaced by different types of signaling devices.

It can be seen that the invention achieves at least all of its stated objectives.

What is claimed is:

1. Means for detecting the presence of electrically conducting fluid comprising:
   a gating means for conducting electrical current through an electrical path upon the introduction of a sufficient triggering voltage;
   a signaling means connected to the gating means and actuated upon conduction of current through the gating means;
   a probe means for placement in a desired location and for detection of fluid having first, second, and third conducting means, the first and second conducting means comprising exposed electrical conductors spaced apart but adjacently positioned, the second and third conducting means comprising exposed electrical conductors which are electrically connected;
   probe extension cable means having first, second, and third electrical conducting wires each connected at one end to the first, second, and third conducting means, respectively;
   a voltage dividing means comprising first and second resistive means, each having first and second electrical connection ends;
   the other end of the first wire being conductingly connected to one side of an electrical power source and the first end of the first resistive means, the other end of the second wire being conductingly connected to the second end of first resistive means, the third wire being conductingly connected to the first end of the second resistive element, and the second end of the second resistive element being conductingly connected to the other side of the electrical power source;
   an electrical conducting wire connected between the second end of the first resistive means and the gating means for supplying the triggering voltage to the gating means; and
   so that in the absence of sufficient electrical conducting fluid between the first and second conducting means, current flows through the first resistive means, the second and third conducting wires, and the second resistive means, causing insufficient triggering voltage to be supplied to the gating means to allow conduction of current through the electrical path to actuate the signal means;
   and so that any damage to the second or third conducting wires to render them non-conducting would remove the resistance of the second resistive means and cause sufficient current and triggering voltage to activate the signal means;
   and so that when sufficient electrical conducting fluid shorts out the first and second conducting means, the resistance of the second resistive means is bypassed and sufficient triggering voltage is supplied to the gating means to allow the conduction of electrical current through the electrical path to actuate the signal means.

2. The means of claim 1 further comprising a non-falsing circuit including a capacitor means, connected in parallel across the second resistive means, for absorbing any surge, reflected pulse or other abnormal electrical signal to the probe means or probe extension cable means when electrical power is first applied to the circuitry of the means for detecting fluid.

3. The means of claim 2 wherein the first and second conducting wires include a conductance between them.

4. The means of claim 3 whereby the value of the capacitor for non-falsing of the circuit is determined by the following equation, $$C_{R2} = 4(R_{R1} \times C_{wires})/R_{R2}$$

where $C_{R2}$ equals the capacitance of the non-falsing capacitor; $R_{R1}$ equals the resistance of the first resistive means; $C_{wires}$ equals the capacitance of the first and second conducting wires; $R_{R2}$ equals the resistance of the second resistive means.

5. The means of claim 1 wherein the electrical current is supplied by an alternating current source.

6. The means of claim 1 wherein the electrical current is supplied by a direct current battery.

7. The means of claim 4 further comprising a battery monitoring circuit for detecting a weakened battery by monitoring circuit voltage including:
   bridge means for dividing the circuit voltage into a voltage proportional to the circuit voltage;
   reference means for producing a reference voltage from the circuit voltage;
   comparator means for comparing the voltage of the bridge means to the reference voltage; and
   signal means for producing a signal when the bridge voltage falls below the reference voltage.

8. The means of claim 1 further comprising a remote alarm interface circuit including a switch which can bypass the signal means and a relay which can cause a remote alarm to be activated upon the conduction of current through the electrical pathway of the gating means.

* * * * *